United States Patent
Guaragno

(10) Patent No.: US 9,937,017 B2
(45) Date of Patent: Apr. 10, 2018

(54) DENTAL HANDPIECE

(71) Applicant: Dentsply Sirona Inc., York, PA (US)

(72) Inventor: Kenneth R Guaragno, Spring Grove, PA (US)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/062,832

(22) Filed: Mar. 7, 2016

(65) Prior Publication Data

US 2016/0317246 A1    Nov. 3, 2016

Related U.S. Application Data

(60) Provisional application No. 62/129,196, filed on Mar. 6, 2015.

(51) Int. Cl.
| | |
|---|---|
| *A61C 1/07* | (2006.01) |
| *A61C 1/14* | (2006.01) |
| *A61C 17/20* | (2006.01) |
| *A61C 3/03* | (2006.01) |

(52) U.S. Cl.
CPC ............... *A61C 1/07* (2013.01); *A61C 1/148* (2013.01); *A61C 3/03* (2013.01); *A61C 17/20* (2013.01)

(58) Field of Classification Search
CPC .. A61C 1/07; A61C 1/148; A61C 3/03; A61C 17/20
USPC .................................. 433/119, 126
See application file for complete search history.

(56) References Cited

U.S. PATENT DOCUMENTS

| | | | | |
|---|---|---|---|---|
| 4,504,227 | A * | 3/1985 | Lohn ..................... | A61C 1/08 433/126 |
| 5,033,960 | A * | 7/1991 | Heil ...................... | A61C 1/088 433/126 |
| 6,227,853 | B1 * | 5/2001 | Hansen ................. | A61C 1/148 279/128 |
| 2002/0009690 | A1 * | 1/2002 | Kuhn ..................... | A61C 1/185 433/105 |
| 2002/0117849 | A1 * | 8/2002 | Bailey .................... | A61C 1/18 285/123.15 |
| 2004/0124631 | A1 * | 7/2004 | Kardeis .................. | A61B 17/1622 285/124.1 |
| 2014/0212833 | A1 * | 7/2014 | Mangelberger ......... | A61C 1/0015 433/80 |
| 2014/0353966 | A1 * | 12/2014 | Schmidt ................. | F16L 33/32 285/330 |

* cited by examiner

*Primary Examiner* — Nicholas Lucchesi
(74) *Attorney, Agent, or Firm* — Leana Levin; Douglas J. Hura; David A. Zdurne

(57) ABSTRACT

A dental handpiece and a dental cleaning procedure are disclosed. The dental handpiece includes an inner barrel for rotatably retaining an ultrasonic insert, the inner barrel configured for contacting the ultrasonic insert with a cooling fluid in the inner barrel, a coil unit arranged and disposed to apply an alternating magnetic field to the ultrasonic insert when positioned in the inner barrel, at least one contact retention clip that contacts a drive coil of the contact unit, an outer sheath extending around at least a portion of the coil unit. The dental handpiece includes flow regions permitting steam, chemicals, and heat to flow into the inner barrel and out of the inner barrel during a sterilization technique. The dental cleaning procedure includes operating the dental handpiece and autoclaving the dental handpiece.

4 Claims, 23 Drawing Sheets

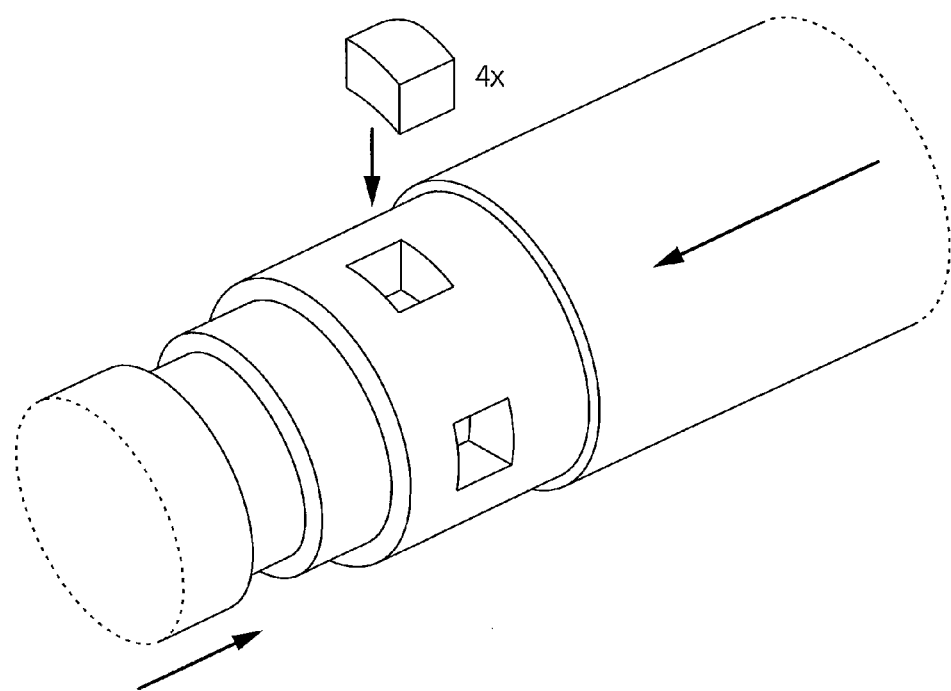
FIG. 40
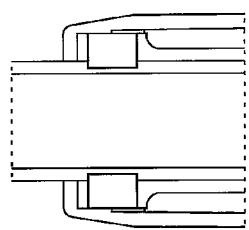
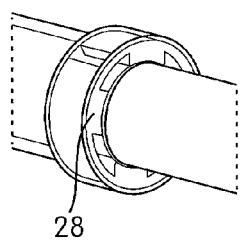
FIG. 41   FIG. 42

DENTAL HANDPIECE

FIELD OF THE INVENTION

The present invention is generally dental medical handpieces, dental medical systems including dental medical handpieces, and processes of using dental medical handpieces. More particularly, the present invention is related to such systems, handpieces, and processes relying upon ultrasonics.

BACKGROUND

An ultrasonic dental tool typically includes a handpiece connected to a cable that has lavage and connects electrical power, ground, and feedback circuits. The cable may include a flexible tube to provide the lavage (for example, water chlorohexidine, and/or mouth wash). The cable connects a scaling unit to the handpiece circuits.

During a typical ultrasonic cleaning procedure, a dentist or hygienist will need to change the direction of an insert tip relative to the lay of the cable in the dental tool in order to properly adapt to the tooth surface being cleaned. Because the insert to handpiece seal is a static seal, it is not easily rotated because of frictional forces (from having a tight fit). Typically, the insert must be removed from a patient's mouth and both hands of the dentist or the hygienist must be used to rotate the tip (for example, moving from mandibular anterior to maxillary premolar). Such action interrupts workflow and, thus, productivity. Without changing the orientation of the tip, the dentist or the hygienist would have to counter the cable's torsional load on the handpiece in order to maintain proper tip angulation, which results in a higher pinch grip force. Tighter pinch grips can be a source of fatigue, reduction in tactile sensitivity, and/or the ability to assure patient comfort.

A dental medical handpiece, dental medical system including a dental medical handpiece, and a process of using a dental medical handpiece that show one or more improvements in comparison to the prior art would be desirable in the art.

BRIEF DESCRIPTION

In an embodiment, a dental handpiece includes an inner barrel for rotatably retaining an ultrasonic insert, the inner barrel configured for contacting the ultrasonic insert with a cooling fluid in the inner barrel, a coil unit arranged and disposed to apply an alternating magnetic field to the ultrasonic insert when positioned in the inner barrel, and an outer sheath extending around at least a portion of the coil unit. The dental handpiece includes flow regions permitting steam, chemicals, and heat to flow into the inner barrel and out of the inner barrel during a sterilization technique.

In another embodiment, a dental handpiece includes an inner barrel for rotatably retaining an ultrasonic insert, the inner barrel configured for contacting the ultrasonic insert with a cooling fluid in the inner barrel, a coil unit arranged and disposed to apply an alternating magnetic field to the ultrasonic insert when positioned in the inner barrel, and an outer sheath extending around at least a portion of the coil unit. The dental handpiece is configured for adjusting torque from a lower torque level to a higher torque level by adjustment of a swivel drag adjustment screw.

In another embodiment, a dental cleaning procedure includes operating a dental handpiece thereby applying an alternating magnetic field to an ultrasonic insert positioned in an inner barrel of the dental handpiece, and autoclaving the dental handpiece, allowing steam to flow through flow regions in the dental handpiece.

Other features and advantages of the present invention will be apparent from the following more detailed description, taken in conjunction with the accompanying drawings which illustrate, by way of example, the principles of the invention.

BRIEF DESCRIPTION OF THE DRAWINGS

FIG. 40 is a perspective view of a portion of an embodiment of a dental handpiece having a body of increasing width to secure a coil unit and an inner barrel according to the disclosure.

FIG. 41 is a perspective view of an incomplete annular structure for securing a coil unit and an inner barrel according to the disclosure.

FIG. 42 is a perspective view of a portion of an embodiment of a dental handpiece having an incomplete annular structure securing a coil unit and an inner barrel according to the disclosure.

DETAILED DESCRIPTION

Provided is a dental handpiece. Embodiments of the present disclosure, for example, in comparison to concepts failing to include one or more of the features disclosed herein, permit exposure to an increased number of sterilization cycles, permit exposure to an increased range of temperature cycles, allow use of autoclaving techniques not previously practicable, reduce or eliminate short-circuits, permit more dentists and hygienists to be more productive, permit more dentists and hygienists to avoid fatigue and injury, generate other suitable advantages that will be apparent from the present disclosure, or a combination thereof.

Figure 1:
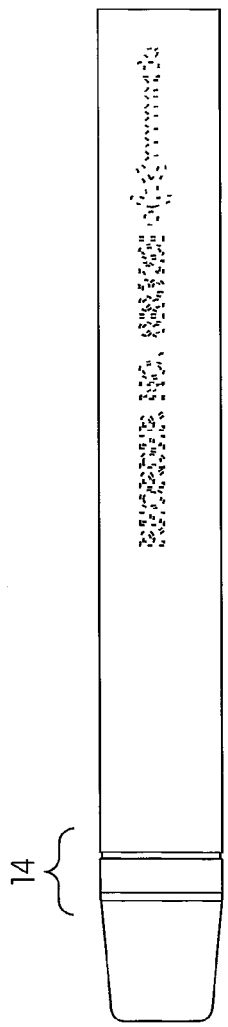
FIG. 1 shows a perspective view of a dental handpiece sheath.
Figure 2:
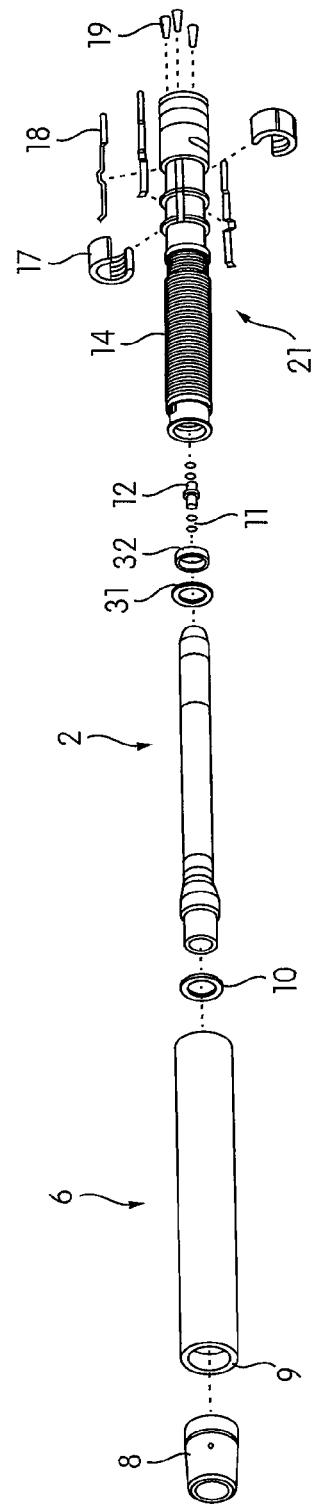
FIG. 2 shows perspective view of a dental handpiece in disassembled form according to an embodiment of the disclosure.
Figure 3:
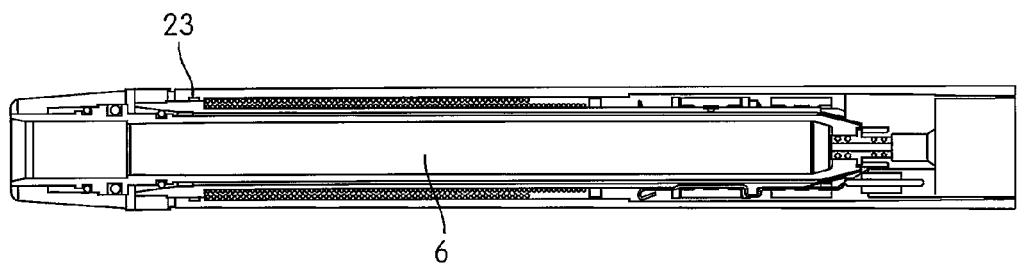
FIG. 3 is a cross-section view of a dental handpiece according to an embodiment of the disclosure.
Figure 4:
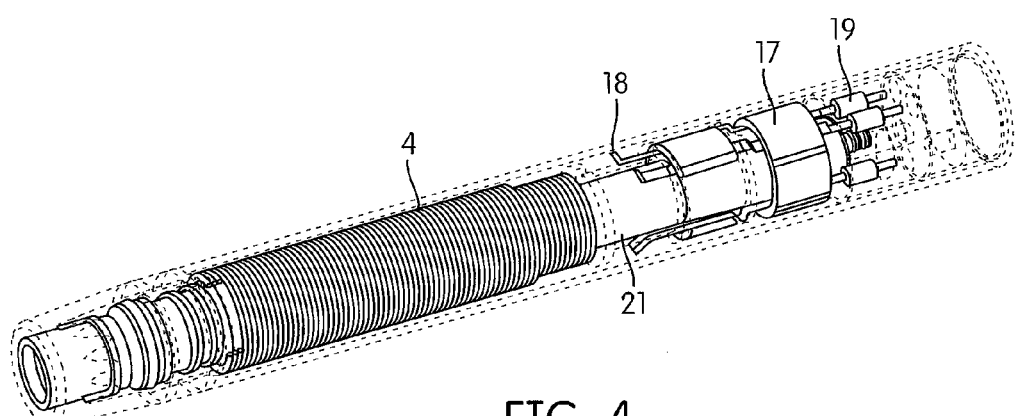
FIG. 4 is a perspective view of a dental handpiece having a coil unit for an embodiment according to the disclosure.
Figure 5:
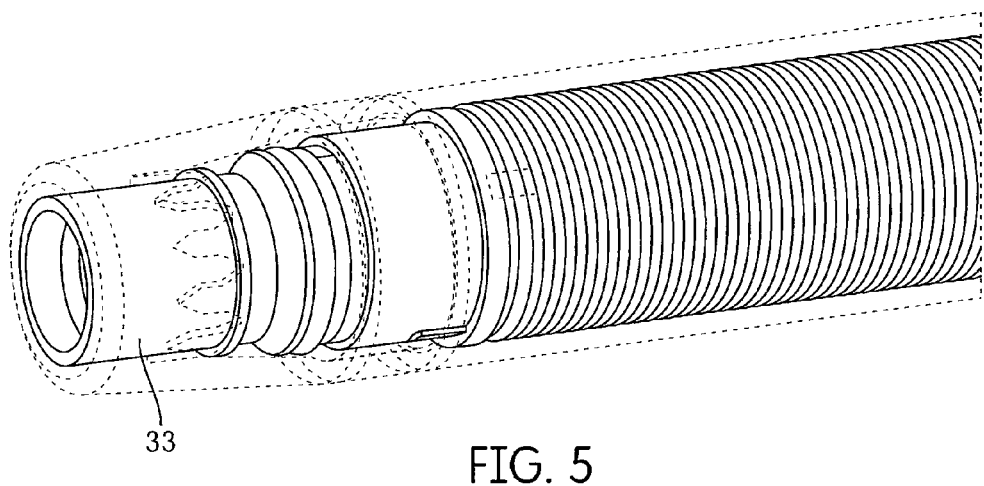
FIG. 5 is a perspective view of a dental handpiece having a coil unit for an embodiment according to the disclosure.
Figure 6:
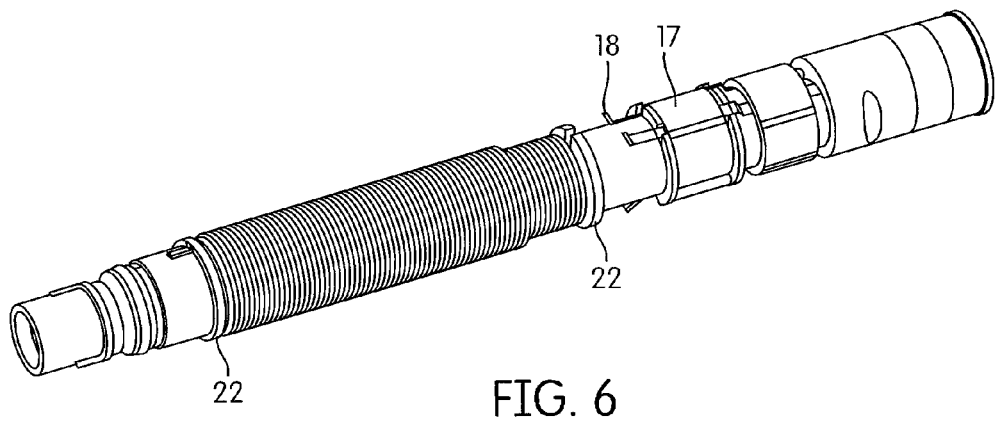
FIG. 6 is a perspective view of a dental handpiece having a coil unit for an embodiment according to the disclosure.
Figure 7:
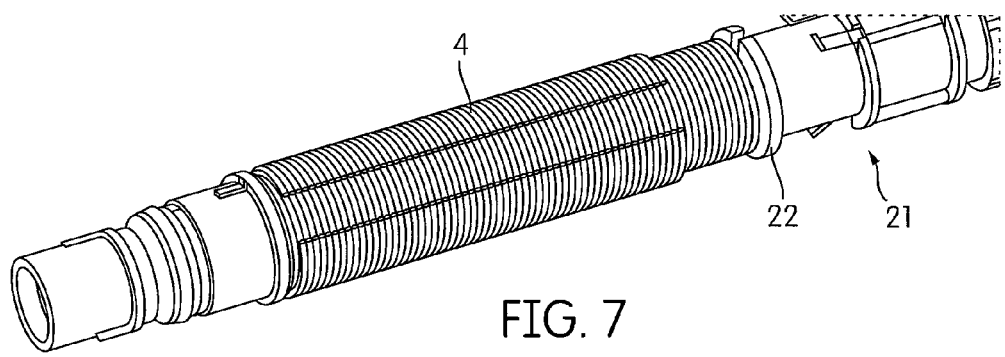
FIG. 7 is a perspective view of a dental handpiece having a coil unit for an embodiment according to the disclosure.
Figure 8:
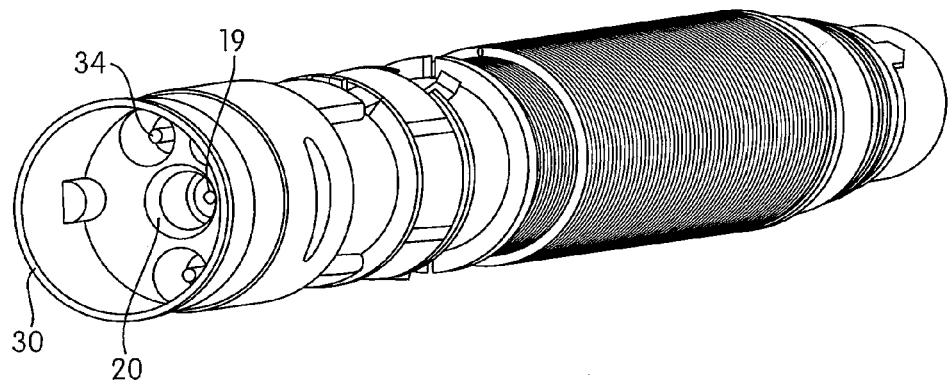
FIG. 8 is a perspective view of a keying feature of a dental handpiece that connects to a power chord.
Figure 9:
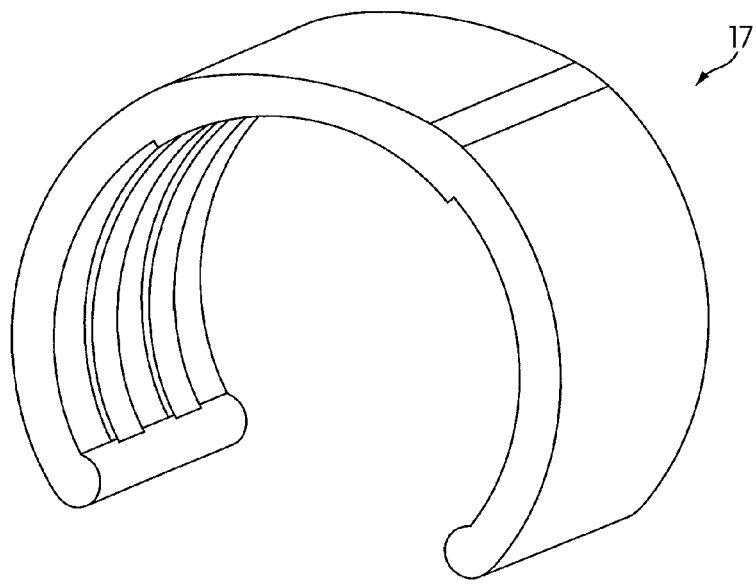
FIG. 9 is an enlarged view of a contact retention clip in a dental handpiece disclosed herein.
Figure 10:
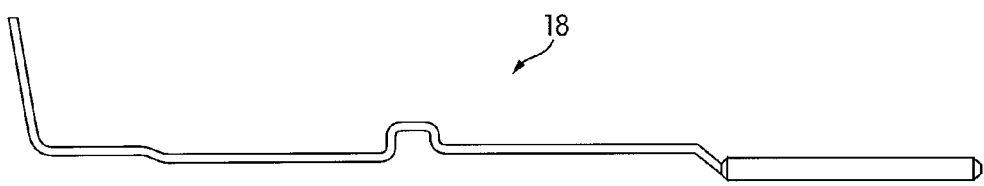
FIG. 10 is an enlarged view of the electrical contact used to terminate the drive coil and provide a mating pin to the cables electrical receptacle contact disclosed herein.
Figure 11:
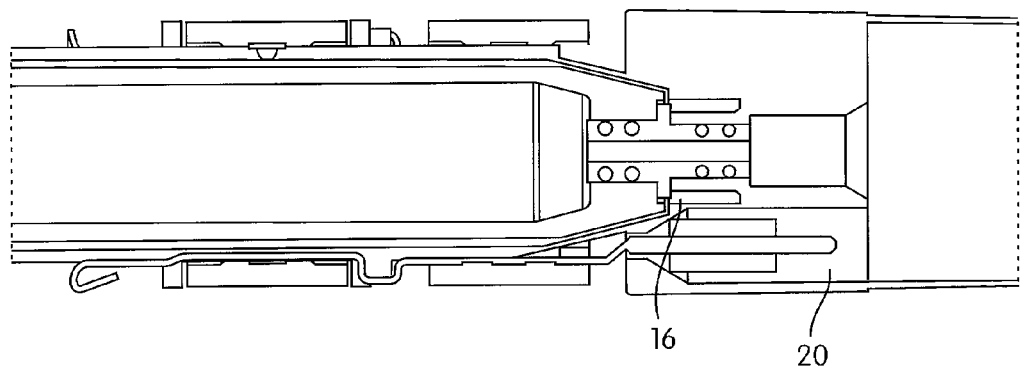
FIG. 11 is an enlarged view of the contact retention clips gripping the coils in a dental handpiece according to an embodiment of the present disclosure.
Figure 12:
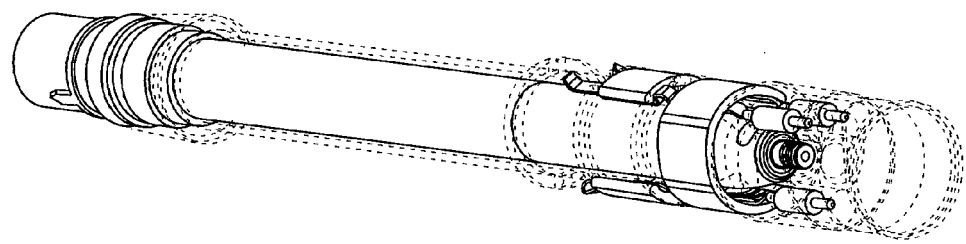
FIG. 12 demonstrates that the contact retention clips keep the electrical contact secure.
Figure 13:
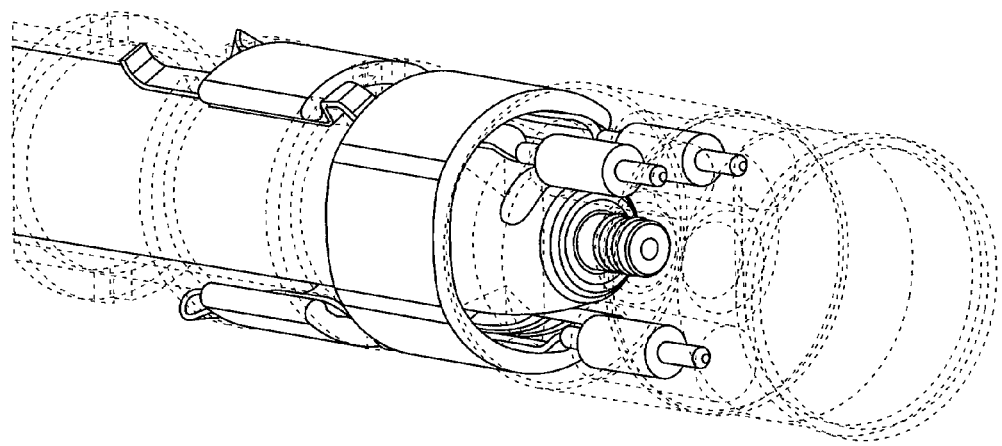
FIG. 13 is an enlarged view of a tubular seal that sits on top of each electrical contact so that when the handpiece is mated to the power cable, these elastomeric tubes are compressed to create a seal that protects the electrical connection from ingress of fluids.
Figure 14:
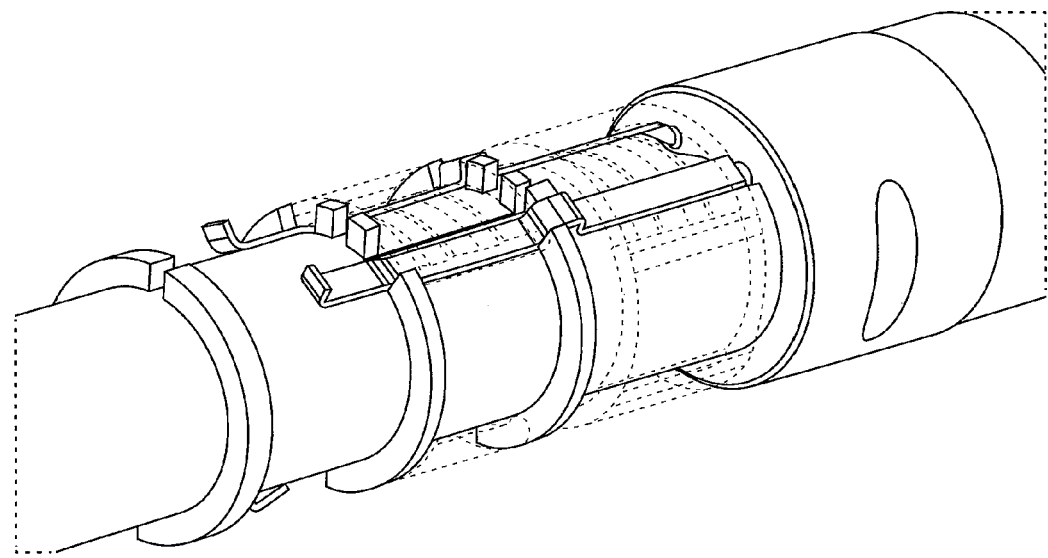
FIG. 14 demonstrates that the contact retention clips keep the electrical contact secure.
Figure 15:
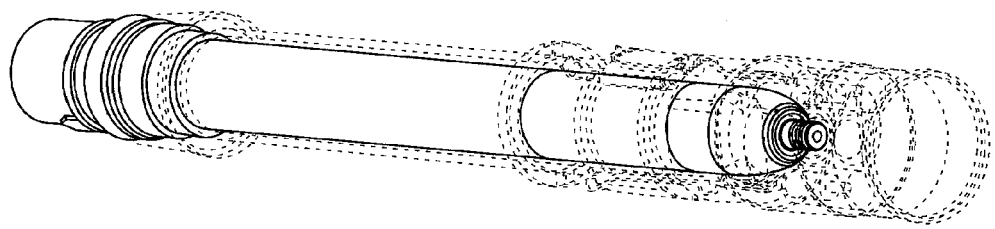
FIG. 15 demonstrates how a inner sheath is enclosed by the coil unit of a dental handpiece according to one embodiment described in the disclosure.
Figure 16:
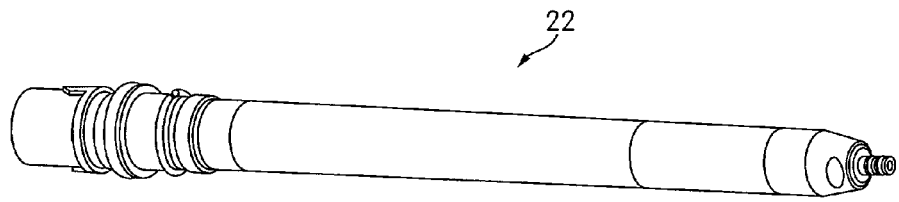
FIG. 16 demonstrates an inner sheath subassembly (with the seal carrier, Teflon bearing, snap-ring, and nose retention o-ring installed) of a dental handpiece according to one embodiment described in the disclosure.
Figure 17:
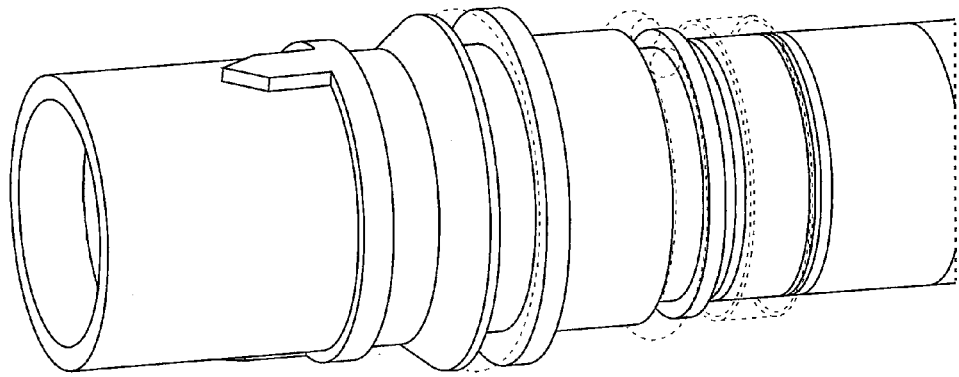
FIG. 17 Enlarged perspective view of distal end of inner sheath providing detail of nose anti rotation feature 33, nose retention o-ring, snap ring 31, and bearing of a dental handpiece according to one embodiment described in the disclosure.
Figure 18:
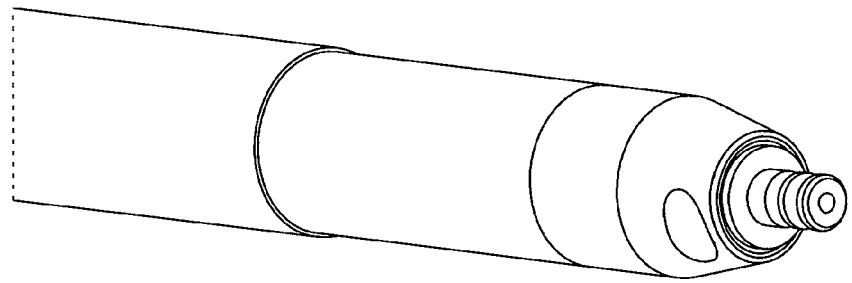
FIG. 18 Enlarged perspective view of proximal end of inner sheath providing detail of seal carrier of a dental handpiece according to one embodiment described in the disclosure.
Figure 19:
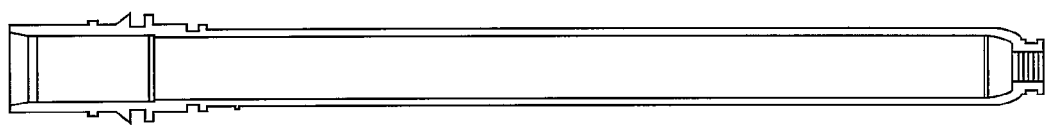
FIG. 19 demonstrates an inner sheath of a dental handpiece according to one embodiment described in the disclosure.
Figure 20:
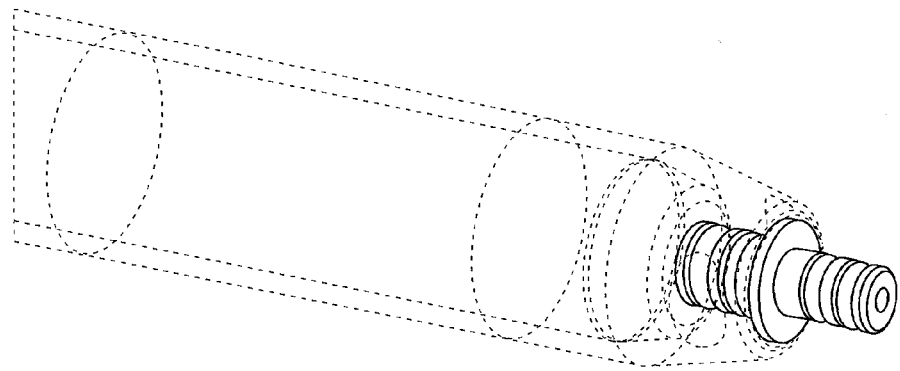
FIG. 20 Enlarged perspective view of proximal end of inner sheath providing detail of static seal portion of seal carrier of a dental handpiece according to one embodiment described in the disclosure.
Figure 21:
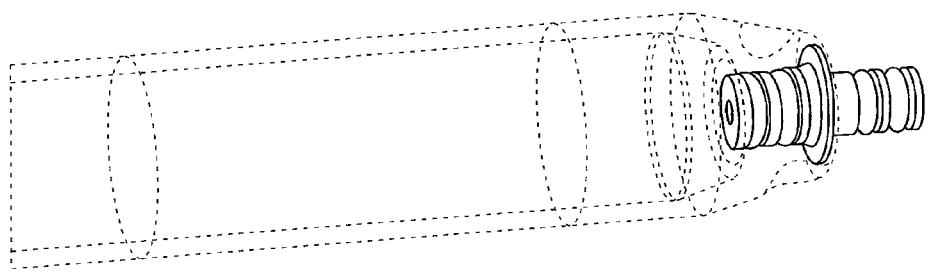
FIG. 21 Enlarged perspective view of proximal end of inner sheath providing detail of static seal portion seal carrier of a dental handpiece according to one embodiment described in the disclosure
Figure 22:
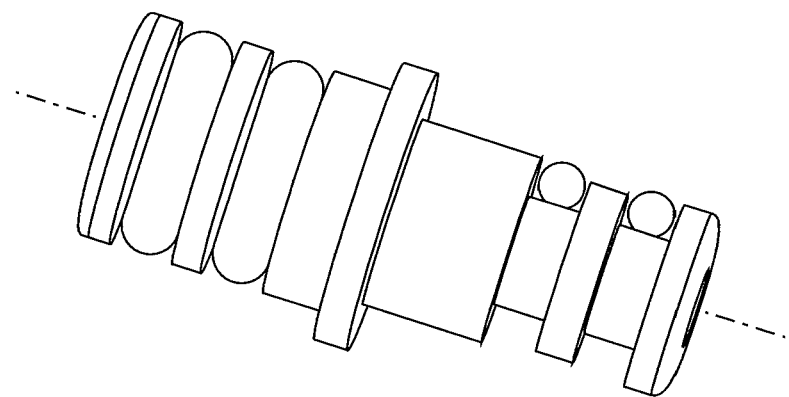
FIG. 22 is an enlarged of a seal carrier.
Figure 23:
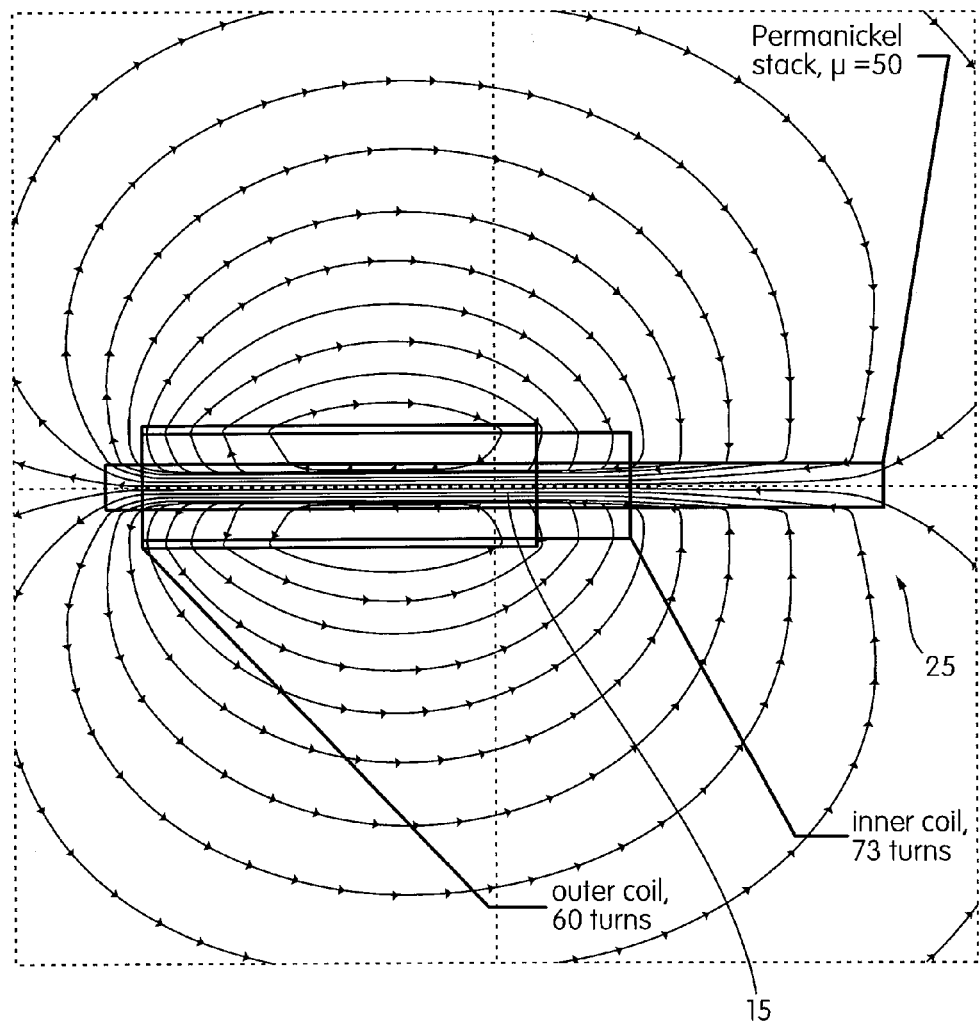
FIG. 23 Electromagnetic field model of the drive coil with permanickle laminate stack of an ultrasonic dental scaler insert providing the magnetic core of a dental handpiece according to one embodiment described in the disclosure.
Figure 24:
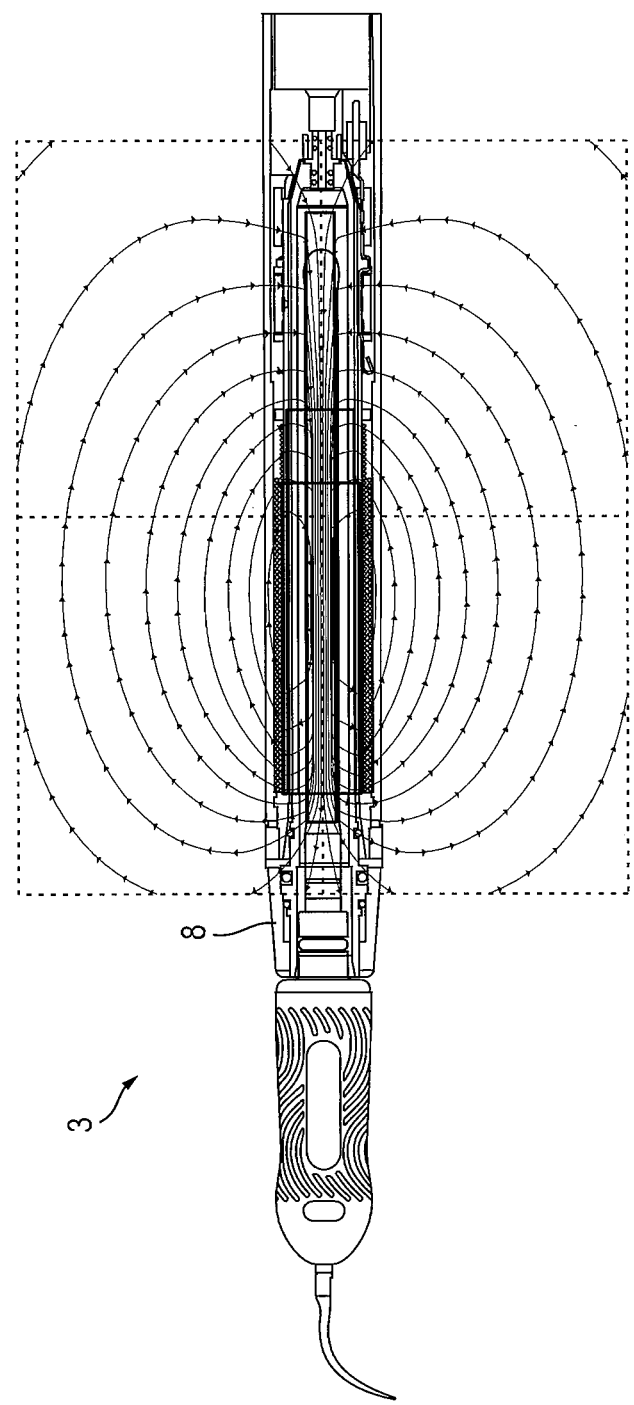
FIG. 24 shows a section view of a dental handpiece according to an embodiment of the disclosure.
Figure 25:
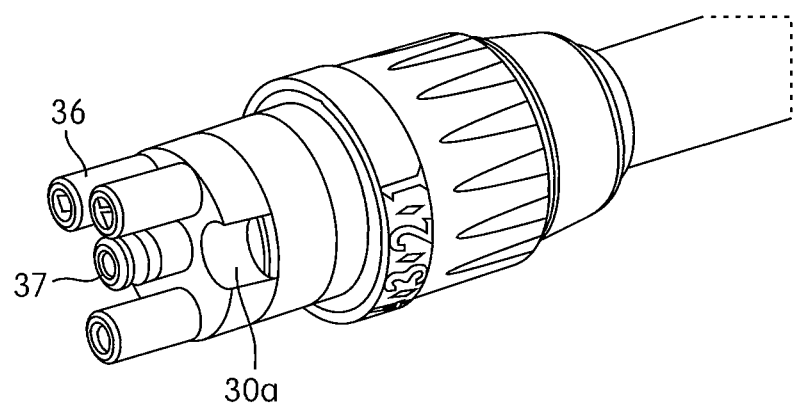
FIG. 25 shows the keying feature on the power chord.
Figure 26:
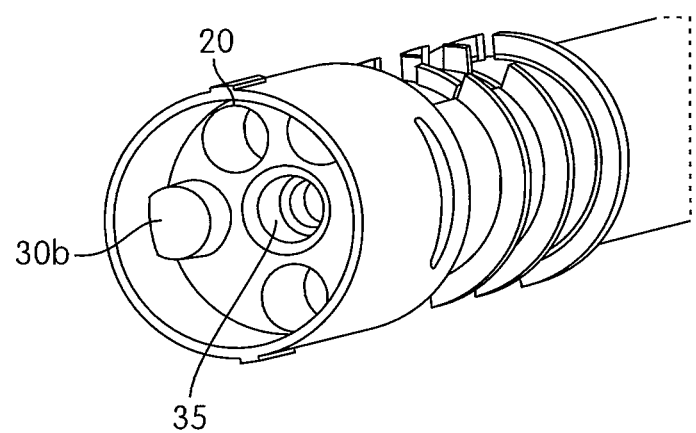
FIG. 26 shows the keying feature on the dental handpiece.
Figure 27:
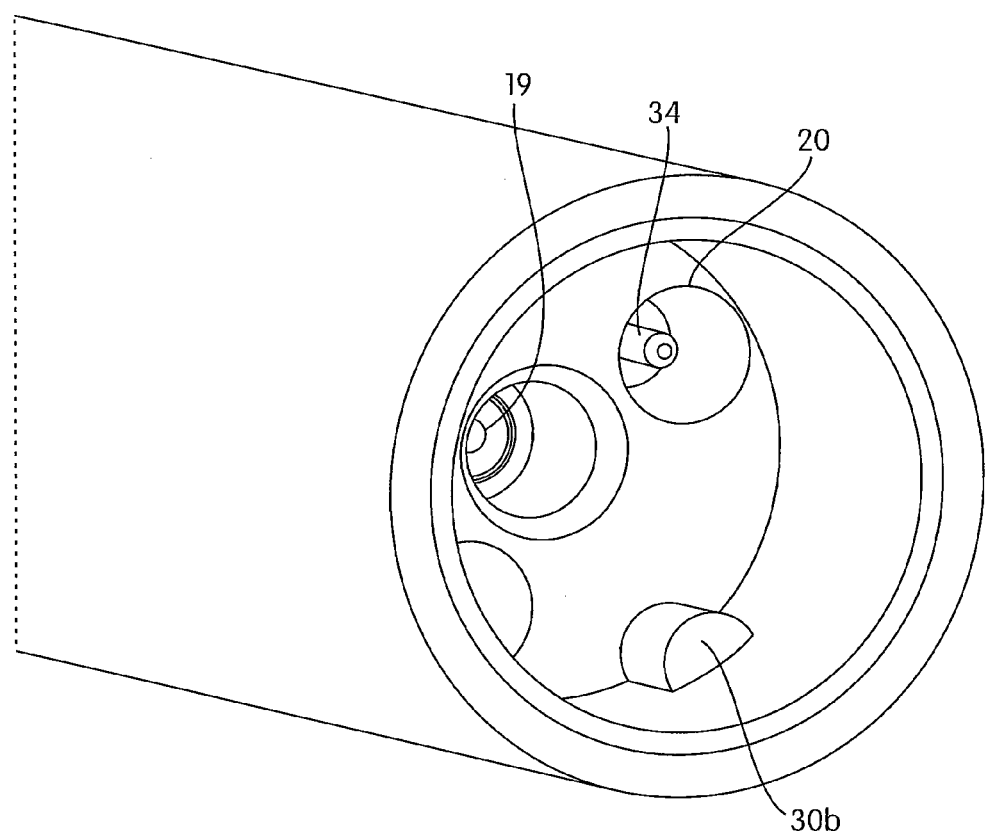
FIG. 27 shows an enlarged view of the keying feature of the dental handpiece.
Figure 28:
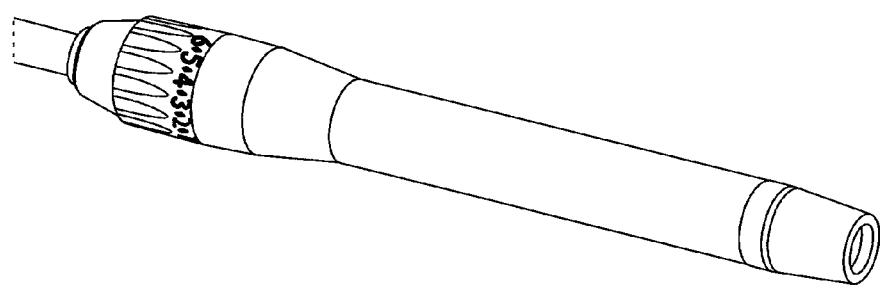
FIG. 28 shows an embodiment where the handpiece can mate with air polishing system.
Figure 29:
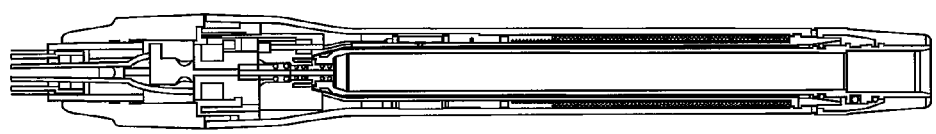
FIG. 29 shows a cross section of the embodiment shown in FIG. 28.
Figure 30:
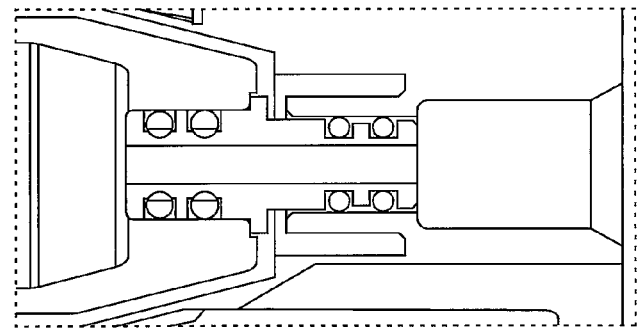
FIG. 30 shows a cross section of a dynamic seal.
Figure 31:
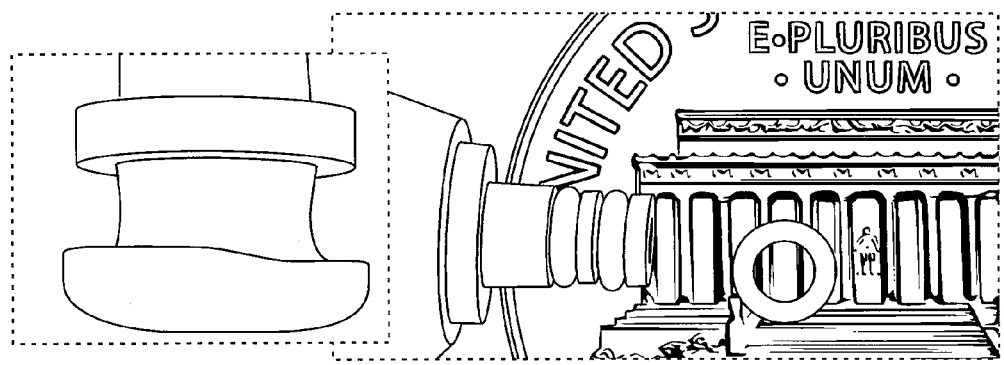
FIG. 31 is another view of the dynamic seal and demonstrates that it can be molded.
Figure 32:
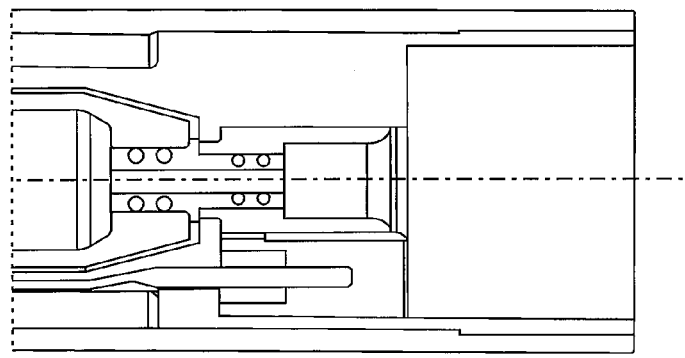
FIG. 32 is another view of the dynamic seal and demonstrates that it can be manufactured.
Figure 33:
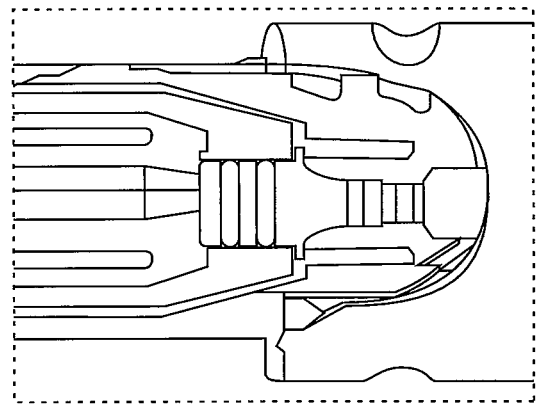
FIGS. 33 and 34 demonstrate a coil form molded hole.
Figure 34:
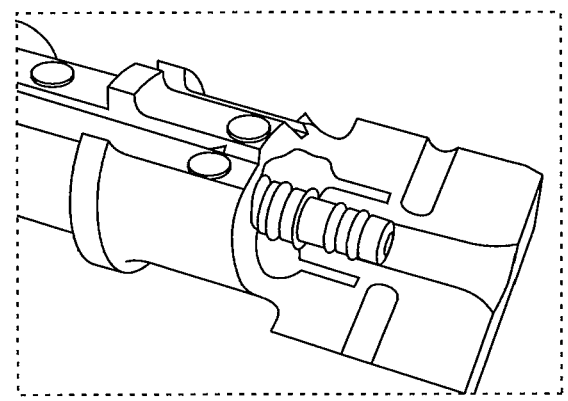
Figure 35:
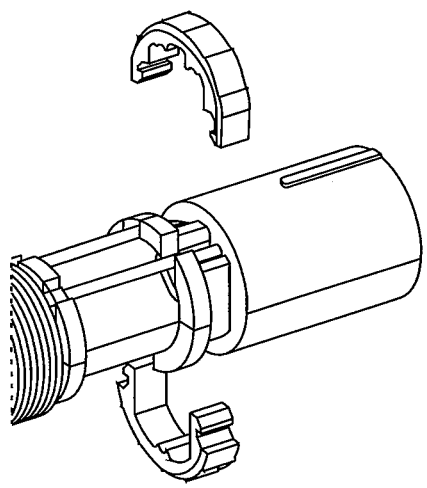
FIGS. 35-37 demonstrate a concept to where the contacts are loaded and use a high durometer elastomeric to hold the contacts into position.
Figure 36:
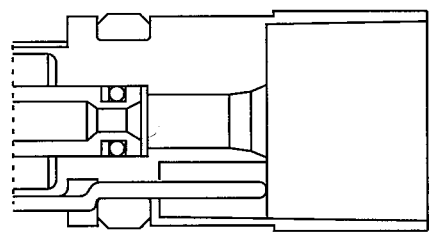
Figure 37:
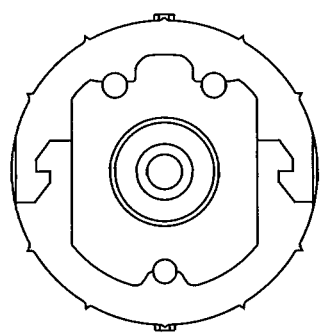
Figure 38:
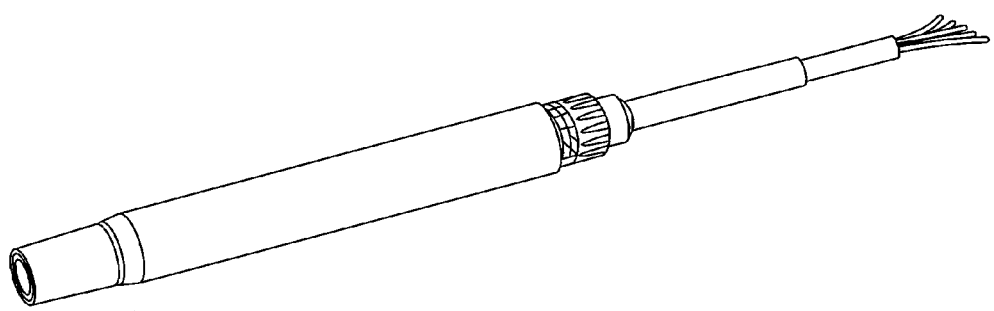
FIG. 38 shows a perspective view of a dental handpiece according to an embodiment of the disclosure.

FIG. 38 shows a dental handpiece capable of being used for supra and sub-gingival treatment, periodontal debridement, endodontic procedures, or other oral procedures. Referring to FIGS. 2 and 24, the dental handpiece 1 includes an inner barrel 2 for rotatably retaining an ultrasonic insert 3 (for example, allowing 360 degree rotation of the ultrasonic insert 3). The inner barrel 2 is configured for contacting the ultrasonic insert 3 with a cooling fluid in the inner barrel 2. The dental handpiece 1 further includes a coil unit 4 arranged and disposed to apply an alternating magnetic field to the ultrasonic insert 3 when positioned in the inner barrel 2, and an outer sheath 6 extending around at least a portion of the coil unit 4. The dental handpiece 1 includes flow regions 5 permitting steam, chemicals, and heat to flow into the inner barrel 2 and out of the inner barrel 2 during a sterilization technique.

The material for the elements of the dental handpiece 1 includes any suitable material capable of withstanding temperature and pressure of autoclaving. Such conditions are those that apply to using steam autoclaves, chemical vapor autoclaving, rapid dry heating, transfer sterilization, dry heating, and/or ultrasonic cleaning, for example, at an operating temperature of 132° C. to 190° C. for 10 to 30 minutes wrapped, followed by 3 to 6 minutes unwrapped, in the presence of chemicals such as formaldehyde and/or alcohol, and/or under cooling/drying conditions for 10-20 minutes. Suitable materials include, but are not limited to, polyetherimide, glass-fiber reinforced materials, amorphous polyamide resin, and/or liquid crystal polymer material.

The outer sheath 6 protects users of the dental handpiece 1 (such as, a dentist or hygienist) as well as those receiving treatment (such as patients), for example, by preventing exposure to electrical contacts 18 and coils, reducing or eliminating biological materials that can lead to infection, and by including surfaces and profiles that allow disinfectant wiping. Additionally, the outer sheath 6 permits ergonomic use of the dental handpiece 1. In general, the outer sheath 6 is tubular and/or cylindrical, with an open interior. The outer sheath 6 includes a larger open end 7 (see FIG. 2) distal from a rotatable nozzle 8 and a smaller open end 9 (see FIG. 2) proximal to the rotatable nozzle 8. In one embodiment, the larger open end 7 is capable of connection/separation from an external cable assembly (not shown) using securing mechanism 10 (see FIG. 24), such as, tabs and grooves within the outer sheath 6. Other suitable securing mechanisms 10 (see FIG. 2) capable of being utilized within the dental handpiece 1 include, but are not limited to, seals (for example, one or more dynamic seals 11), bearing 32s, clips, rings, retainers, other features that permit disassembly of the dental handpiece 1, other features that facilitate removal of debris within the dental handpiece 1, or a combination thereof. The dynamic seal 11 is made of a compliant member (for example, an o-ring, a lip seal, or the like) and a seal carrier 12 (for example, a machined or molded component, or the like). The seal carrier 12 is manufactured to have a low friction, high integrity surface free of defects, such that the seals can rotate over the seal carrier 12 with little to no friction and resultant wear. The seal carrier 12 can be made of any suitable compliant material, such as Teflon®, so that small degrees of misalignment or side loading can be absorbed and not transferred in the seals generated uneven loading and potential loss of compression resulting in leakage. In an embodiment including one of the dynamic seals 11 positioned proximal to the smaller open end 9, the dynamic seal 11 has a diameter that is ⅓ or less in length in comparison to the diameter of the outer sheath 6, thereby reducing friction between the dynamic seal 11 and rotating surface of the dental handpiece 1, allowing for less drag during operation of the dental handpiece 1, allowing for smoother operation of the dental handpiece 1, and/or allowing for operation with torque of less than 1 in oz or ½ in oz or 0.01 in-oz, with torque being defined by the following equation:

$$\text{Torque} = \mu R_S R_L \qquad \text{(Equation 1)}$$

Figure 45:
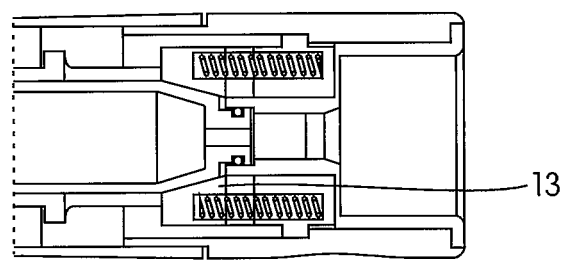
FIG. 45 is a side view of an embodiment of a dental handpiece having a dampener according to the disclosure.
Figure 46:
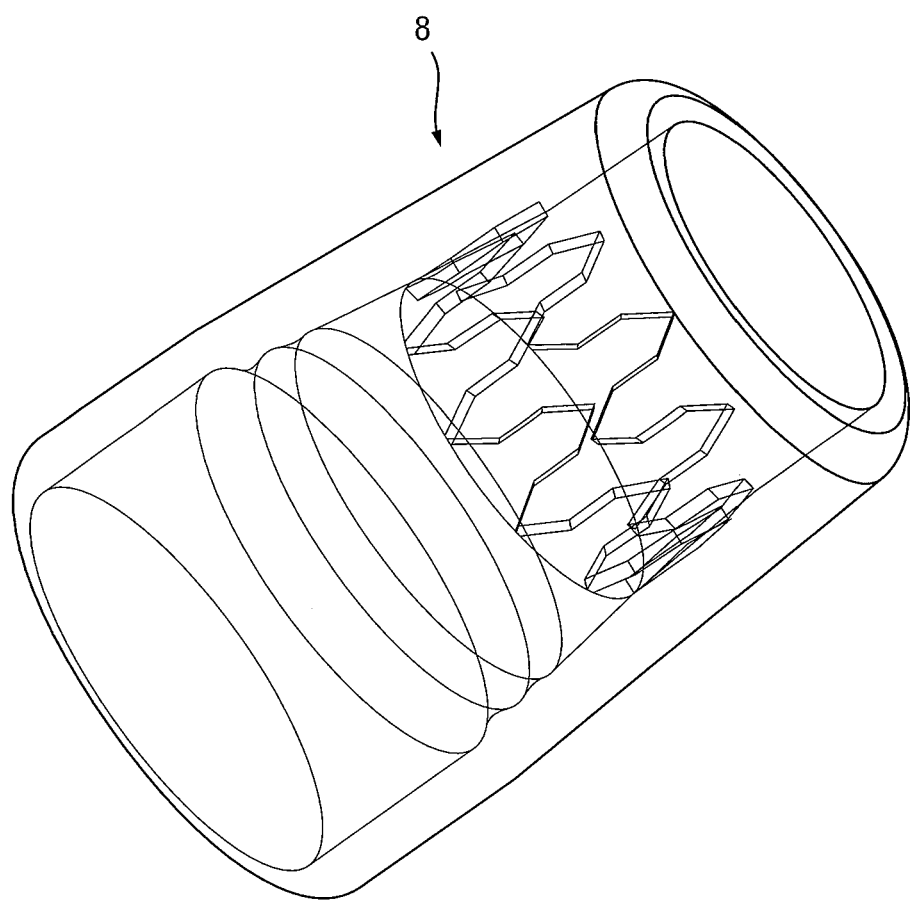
FIG. 46 is a perspective view of the nose showing the anti-rotation features 33. The nose is removable to aid the clinician in cleaning, during installation the nose automatically interlocks with the inner sheath to prevent it from rotating relative to the inner sheath. The inner sheath and the nose become fixed both axially and radially so that forces applied to the nose during use are coupled to the inner sheath.

According to the above equation, $\mu$ refers to the coefficient of friction for the dynamic seal 11, $R_S$ refers to the radius of the seal carrier 12, and $R_L$ refers to axial loading. Referring to FIG. 45, in one embodiment, the dental handpiece 1 includes a dampener 13 extending around the coil unit 4 for balancing/equalizing pressure on the dynamic seal 11.

In one embodiment, the outer sheath 6 has limited or no crevices that permit bacteria or other biological materials to grow. For example, in one embodiment, the dental handpiece 1 is manufactured such that crevices exist only in flow regions 5, such as, in the larger open end of the dental handpiece distal from the rotatable nozzle 8. In a further embodiment, the flow regions 5 are formed by ribs or by a loose abutting fit between elements of the dental handpiece 1. The flow regions 5 have any suitable dimensions. In one embodiment, the flow regions 5 are between 0.01 mm and 0.5 mm, between 0.02 mm and 0.35 mm, at about 0.25 mm, or any suitable combination, sub-combination, range, or sub-range therein. In a further embodiment, the flow regions 5 include at least two separate paths from outside of the dental handpiece 1 to the interior of the dental handpiece 1.

In embodiments including materials having different coefficients of thermal expansion, crevices defining the flow regions 5 provide sterilization passageways or openings, allowing fluid and heat into the interior of dental handpiece 1 in order to sterilize the inner workings of the handpiece. In one embodiment, the outer sheath 6 has a first coefficient of thermal expansion and the coil unit 4 has a second coefficient of thermal expansion, the first coefficient of thermal expansion differing from the second coefficient of thermal expansion (CTE).

Examples of CTE's are as follows:
Coil form material: Glass fiber reinforced engineering thermoplastic material based on a combination of semicrystalline Polyamide with partially aromatic copolyamide. 23.0-55.0° C.
Coefficient of Thermal Expansion (Parallel) 9.00E–05/° K
Coefficient of Thermal Expansion (Normal) 1.50E–05/° K
Coil: Copper
20.0-100° C. 16.4 µm/° K In a further embodiment, the difference between the coefficients of thermal expansion is above a "fracture value," the "fracture value" being a point where fixed/adhesive coupling would have damaged one or both of the outer sheath 6 and the coil unit 4 during the flow of fluid and/or heat during the sterilization technique, for example, by cracking or fracturing the outer sheath 6. In this embodiment, the outer sheath 6 and the coil unit 4 are not damaged during the flow of the fluid and/or the heat during the sterilization technique, despite such a difference between the coefficients thermal expansion being above the fracture value.

The outer sheath 6 extends around the inner barrel 2. The inner barrel 2 forms a seal with the outer sheath 6 abutting one or more of the securing mechanisms 10, such as, o-rings, or dynamic seals 11. In one embodiment, proximal to the larger open end 7 of the outer sheath 6, the securing mechanism 10 is a dynamic seal 11 that creates a lower amount of drag on ultrasonic insert 3 in comparison to draft on other elements from other seals within the dental handpiece 1. The dynamic seal 11 permits the cooling fluid to flow from being proximal to the larger open end 7 to being proximal to the smaller open end 9, while within the ultrasonic insert 3, prior to cooling and exiting a scaler (such as, a 30 kHz magnetorestrictive scaler) positioned within the rotatable nozzle 8.

Figure 44:
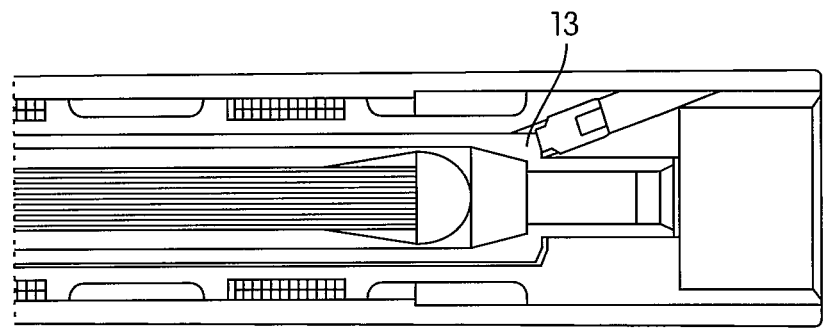
FIG. 44 is a side view of an embodiment of a dental handpiece having a swivel drag adjustment screw according to the disclosure.

The rotatable nozzle 8 extends from the inner barrel 2, for example, through a grip region 14. The grip region 14 includes a material, such as, an elastomeric material, for handling by the user. In one embodiment, the scaler and/or the ultrasonic insert 3 is/are selectively rotatable, capable of being locked in a fixed position, configured for operation at different torque levels (for example, at a lower torque level and a higher torque level), or a combination thereof in response to application of a force (such as a torsional load) to the grip region 14. Alternatively, other suitable dental devices are included instead of the scaler. Referring to FIG. 44, in one embodiment, the torque is adjusted from the lower torque level to the higher torque level by rotating a swivel drag adjustment screw positioned to extend from within the dental handpiece 1 to outside of the dental handpiece 1 where it is adjustable by the dentist or the hygienist. Other suitable mechanisms for torque adjustment include knobs (for example, extending around the outer sheath 6), buttons, clutch assemblies, preloaded barrels, and/or combinations of large and fine adjustment knobs.

The coil unit 4 is within the outer sheath 6 of the dental handpiece 1, for example, being movably secured therein. In one embodiment, the coil unit 4 is capable of being secured within the outer sheath 6 (see FIG. 2) by having alignment members 16 and/or one or more retaining elements (for example, coupling pins), one or more alignment regions (for example, channels corresponding with the coupling pins), one or more mating sockets (not shown) in the cable assembly (not shown), flanges, molded receptacles, other suitable alignment devices, or a combination thereof.

The coil unit 4 generates the magnetic field that oscillates the ultrasonic insert 3 and, thus, the scaler. In one embodiment, the coil unit 4 includes a coated coil wire to extend around the ultrasonic insert 3 (or the region where the ultrasonic insert 3 is to be positioned). The coating reduces or eliminates shorting of the coil unit 4 during the generation of the magnetic field.

The coil unit 4 includes other suitable elements, such as a contact retaining clips 17 extending from a drive coil in electrical communication with electrical contacts 18, which are capable of being the coupling pins. The drive coil conducts electricity from an alternating current source (not shown) that generates the magnetic field. The drive coil is secured to a coil form which serves as a base structure for the coil unit 4, for example, between flanges. Wires within the drive coil are connected to terminals that provide power to the drive coil.

The contact retention clip 17 grips the coil form 21 and keeps the contacts from moving so that during mating and unmating of the handpiece the contacts cannot shift which would result in a loss of concentricy, fatigue of the solder joint, axial movement preventing engagement, and overall loss of integrity. The coil form 21 and the contact engage so that the contact cannot shift axially while the contact-retaining—clip 17 holds the contact tight against the coil form 21 features.

The contact retention clips 17 keep the electrical contacts 18 secure. While a small tubular seal 19 that sits on top of each electrical contact and resides in a molded cavity 20 that is part of the coil form 21. When mated to the cable these elastomeric tubes (e.g. silicone rubber) are compressed creating a seal that protects the electrical connection from the ingress of fluids that might cause corrosion or build-up of residue preventing a reliable connection.

The purpose of the clips is to retain the contacts. The clips stress relax during steam autoclaving to prevent distortion in the coil form 21 that may result in a loss of clearance between the inner barrel 2 and the coil form 21 due to creep. The clips, coil form 21, contacts, and outer sheath 6 once fully assembled provide a mechanical interlocking mechanism that provides contact retention without any clamping force or need for adhesives or bonding agents. The clips maintain their position over the contacts between molded flanges 22 in the coil form 21 and cannot be released from the coil form 21 once the outer sheath 6 is assembled creating a mechanical interlock. The outer sheath 6 latches to the coil form 21 with a positive radial latching mechanism 23 the inside wall of the outer sheath 6 confines the clips so that they cannot back-off of the electrical contacts 18. The flanges of the coil form 21 locate the clips and the form 21 of the contacts create an interlock with molded features in the coil form 21. As a result these seven loose pieces can be assembled and positively locked together without any adhesive or bonding operation.

The contacts have a special form that interlocks them with molded features in the coil form 21. This form prevent the contacts from shifting along their axis when experiencing the mate and unmate forces from the receptacle contact located in the cable's connector. The clip is design to snap onto the coil form 21 and over the contacts so that the contacts cannot lift up out of their retention slots. Two clips are used, one will cover two contacts and the second clip will cover the third contact. Although the handpiece only has one coil three contacts are used, the retention of the handpiece to the cable is achieved through contact normal force generated by the cable connectors receptacle contact, this norm force produces a clamping action on each of the three pins providing adequate retention of the handpiece to the cable.

The retention clips 17 are designed to clamp on to the coil form 21. Their geometry and features aid in their assembly while also providing a predictable amount of clamping force and line-to-line contact over the electrical contacts 18. This both stabilized the contacts in their location and provides a positive retention of the clip prior to the entire subassembly being mated with the outer sheath 6.

The drive coil is attached to the terminal using a right-hand turn, for example, being wound from the flange to the flange and back. The contacts are formed with an extended flat region that can be bent and wrapped around the ends of the drive coil. The drive coil and electrical contact are folded onto themselves creating a mechanical interlock, this joint is then soldered to form a secure electrical and mechanical connection. The contact retention clips 17 secure both the electrical contacts 18 and isolate the drive coil from external mechanical forces that might occur during the mating and unmating of the handpiece. The combination of the contact termination, contact profile engagement with the coil form, and the contact retention clip provide rigidity that prevents the coil from becoming loose due to thermal cycling experienced during autoclave cycling. In one embodiment, the dental handpiece 1 is devoid of potting. Being devoid of potting further permits steam, chemicals, and/or heat to pass into and out of the interior of the dental handpiece 1, allows for the heating and cooling expansion and contraction of parts of different coefficients of thermal expansion without the developing electrical short-circuits, and allows sterilization of the dental handpiece 1.

The drive coil construction, location relative to the insert 3, number of turns, inside diameter, length, and wire gauge in combination with the laminated stack of an ultrasonic insert 3 form an electromechanical transducer 25. The resonant frequency of the transducer 25 (handpiece and ultrasonic insert 3) can be determined by generated a magnetic field that varies in amplitude sinusoidally at or near the mechanical resonance of the ultrasonic insert 3. This is achieved by passing a current through the drive coil. The drive current has both an AC and DC component. The DC component, DC bias, assures that the permanickel stack of the insert 15 is operated in its linear region. The AC component imparts a mechanical vibration in the permanickel 15, the electronics that generate this drive current are capable of locating an optimum operating frequency without the need for a feedback voltage signal. A digital system capable of exciting the handpiece and capturing its response, by monitoring both the drive voltage and current, over a range of frequencies is capable of identifying the transducers 25 optimum operating frequency. The single drive coil and the digital drive circuit combined eliminate the need for both a feedback and bucking coil.

According to one embodiment, the dental handpiece 1 is assembled by an initial assembly of the inner barrel 2 with the securing mechanisms 10, for example, bearing 32s, in the larger open end 7 and the small open end 9, and an initial assembly of the coil unit 4. The inner barrel 2 and the coil unit 4 are then secured together, for example, by being locked/snapped together.

Figure 39:
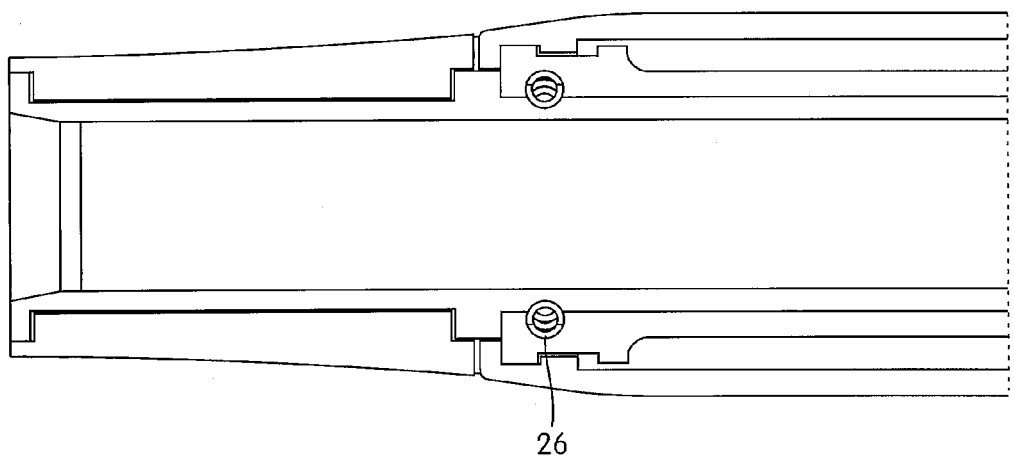
FIG. 39 is a side view of a portion of an embodiment of a dental handpiece having a canted coil spring securing a coil unit and an inner barrel according to the disclosure.

As shown in FIG. 39, in one embodiment, the inner barrel 2 and the coil unit 4 are removably secured by a canted coil spring 26 positioned between the inner barrel 2 and the coil unit 4. In a further embodiment, a non-toxic compatible lubricant, such as food-grade silicone or Teflon®, is included in contact with the canted coil spring 26.

As shown in FIG. 40, according to an embodiment, one suitable technique for securing the inner barrel 2 and the coil unit 4 or for securing other elements of the dental handpiece 1 includes positioning bodies having an increasing width (for example, based upon a first width being smaller than a second width along an insertion direction) into open regions in a direction perpendicular to the insertion direction prior to insertion of the coil unit 4.

Figure 43:
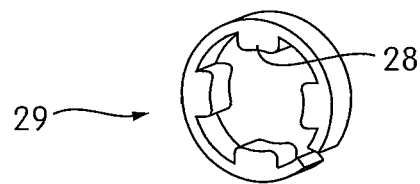
FIG. 43 is a perspective view of an incomplete annular structure for securing a coil unit and an inner barrel according to the disclosure.

Referring to FIGS. 42 and 43, according to one embodiment, a technique for securing the inner barrel 2 and the coil unit 4 or for securing other elements of the dental handpiece 1 includes an incomplete annular structure 28 that has protruding portions 29 and is capable of compression during insertion of the coil unit 4, for example, by having a disconnected opening.

After securing the inner barrel 2 and the coil unit 4, the assembly of the inner barrel 2 and the coil unit 4 is inserted into the outer sheath 6, for example, such that the flanges of the coil form engage the interior wall (not shown) of the outer sheath 6, for example, by frictionally locking. The rotatable nozzle 8 is then secured to the remaining portions of the assembly to produce the dental handpiece 1. Upon being assembled, the dental handpiece 1 is then capable of coupling and operation with a system (not shown) capable of operating the dental handpiece 1. An instrument, such as, the scaler is then capable of being inserted during operation of the dental handpiece 1 by the dentist or hygienists, as described above.

The keying feature prevents the swivel handpiece from mating with older Cavitron® systems that require a feedback coil to operate. However, newer systems that do not require a feedback coil can operate older non-swivel handpiece designs. The keying features do not allow the cable connector to fully engage the handpiece connector preventing a mechanical connection, an electrical connection, and a fluid connection. The keying feature was deliberately designed as a positive element on the handpiece side of the connection so that older handpieces could be mated to newer systems that have a female keying feature. The keying feature can be round, oval, a semi-circle element, one feature, two or more features that engage a similar but reciprocal profile on the other half of the connection. The connector makes at least one electrical connection, such as two or three electrical connections, and one fluid connection. The three electrical contacts provide a secure mechanical retention of the handpiece.

The medical device disclosed herein has a wire end that connects to the handpiece via the handpiece end. Both the wire end and the handpiece end include a keying feature that can be mated together. For example, the wire end may include a female key portion 30a that can mate with the male key portion 30b of the handpiece end. As one of ordinary skill in the art can understand the female key portion could be found on the handpiece end, while the male key portion could be found on the wire end. The wire end includes a receptacle contacts 36 that mate with electrical pins 34 of the handpiece end. This mating between the receptacle contacts 36 and electrical pins 34 provides the electrical power to the medical device as a whole. This electrical mating is separately maintained from the fluid mating of the medical device. The wire end further includes a fluid fitting 37 that mates with the fluid port 35 of the handpiece end. This allows for the fluid, such as water, to travel from outside the medical device through the fluid fitting 37, into the fluid port 35, and further into the fluid chamber of the medical device.

The handpiece disclosed herein has a single coil and only requires two electrical connections, however by maintaining the third electrical connection other modalities may be introduced. The basic concept is driven by the fact that with 2-wire ultrasonic technology we now have a third connection that can be used to deliver a new feature or utility. Some potential concepts:
1. Add a boost LED indicator into the handpiece or flow control, so that boost or tap-on mode can be displayed with an indicator light without the need to look at the unit.
2. We could control power or add a turbo button.
3. Deliver power for a lighted insert (a coil in the handpiece could power a coil in the insert), this is a closed system.
4. Temperature monitoring of the handpiece that provided information for controlling flow and tip temperature. (IP will have to be considered)
5. Add a UV light for water purification or an ozone generator for disinfection of periodontal pockets.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:
1. A dental handpiece, comprising:
   an inner barrel for rotatably retaining an ultrasonic insert, the inner barrel constructed to enclose a fluid chamber and to contact the ultrasonic insert with a cooling fluid in the inner barrel;
   a coil unit arranged and disposed to apply an alternating magnetic field to the ultrasonic insert when positioned in the inner barrel;
   at least one contact retention clip that contacts a drive coil of the coil unit;
   an outer sheath extending around at least a portion of the coil unit,
   wherein a bucking coil and feedback coil are not present.
2. The dental handpiece according to claim 1, wherein power is received through a wire end that mates with an end of the handpiece.
3. The dental handpiece according to claim 2, wherein a first key portion of the wire end mates into a second key portion of the handpiece end.
4. A medical device configuration having a wire end and a medical device end, comprising:
   a first key portion in the wire end,
   a second key portion in the medical device end,
   the wire end comprising receptacle contacts and a fluid fitting,
   the medical device end comprising a fluid port and at least one electrical pin in a molded cavity,
   wherein the receptacle contacts mate into the molded cavity thereby contacting the at least one electrical pin,
   wherein the fluid fitting mates into the fluid port, and
   wherein the first key portion mates with the second key portion.

* * * * *